United States Patent [19]

Callan

[11] Patent Number: 4,656,865
[45] Date of Patent: Apr. 14, 1987

[54] SYSTEM FOR ANALYZING PERMEATION OF A GAS OR VAPOR THROUGH A FILM OR MEMBRANE

[75] Inventor: Lawrence W. Callan, Antioch, Calif.

[73] Assignee: The Dow Chemical Company, Midland, Mich.

[21] Appl. No.: 774,107

[22] Filed: Sep. 9, 1985

[51] Int. Cl.$^4$ ............................................. G01N 15/08
[52] U.S. Cl. ......................................................... 73/38
[58] Field of Search ....................... 73/1 G, 61.3, 64.2, 73/64.3, 19, 38

[56] References Cited

U.S. PATENT DOCUMENTS

| | | | |
|---|---|---|---|
| 3,498,110 | 3/1970 | Brun | 73/38 |
| 3,561,254 | 2/1971 | Argaud et al. | 73/38 |
| 3,590,634 | 7/1971 | Pasternak | 73/64.3 |
| 3,618,361 | 11/1971 | Stephens et al. | 73/38 |
| 3,844,940 | 10/1974 | Kopf et al. | 73/64.3 |
| 3,976,450 | 8/1976 | Marcote et al. | 73/1 G |
| 4,036,915 | 7/1977 | Lucero et al. | 73/1 G |

OTHER PUBLICATIONS

Kolbezen et al, *Pesticide Science*, vol. 3, pp. 67-71, 73-80, (1972).
Kolbezen et al, (Private Paper), pp. 476-481.

*Primary Examiner*—Stewart J. Levy
*Assistant Examiner*—Robert R. Raevis
*Attorney, Agent, or Firm*—Norman L. Sims

[57] ABSTRACT

The invention is a system for measuring the permeation of a vapor or gas through a film or membrane. The device comprises a test cell which has two chambers which are separated by a membrane through which the permeation of a particular gas is measured. To one cell is fed a test gas or vapor either alone or in a mixture with a bulk gas. To the other side of the membrane is fed a bulk gas into which the permeating test gas or vapor permeates. Attached to the second chamber of the test cell is a means for analysis of the concentration of the test gas or vapor. This device further comprises a means for separately controlling the pressure in each chamber of the test cell. The device comprises a means for combining a portion of the bulk gas with the test gas or vapor in a manner such that the concentration of the test gas or vapor in the bulk gas can be carefully controlled. This means of combining the two gases is connected to the first chamber of the test cell. This system allows for the measurement of the permeation of a particular test gas or vapor through a particular membrane at widely varied temperature and pressure conditions.

11 Claims, 1 Drawing Figure

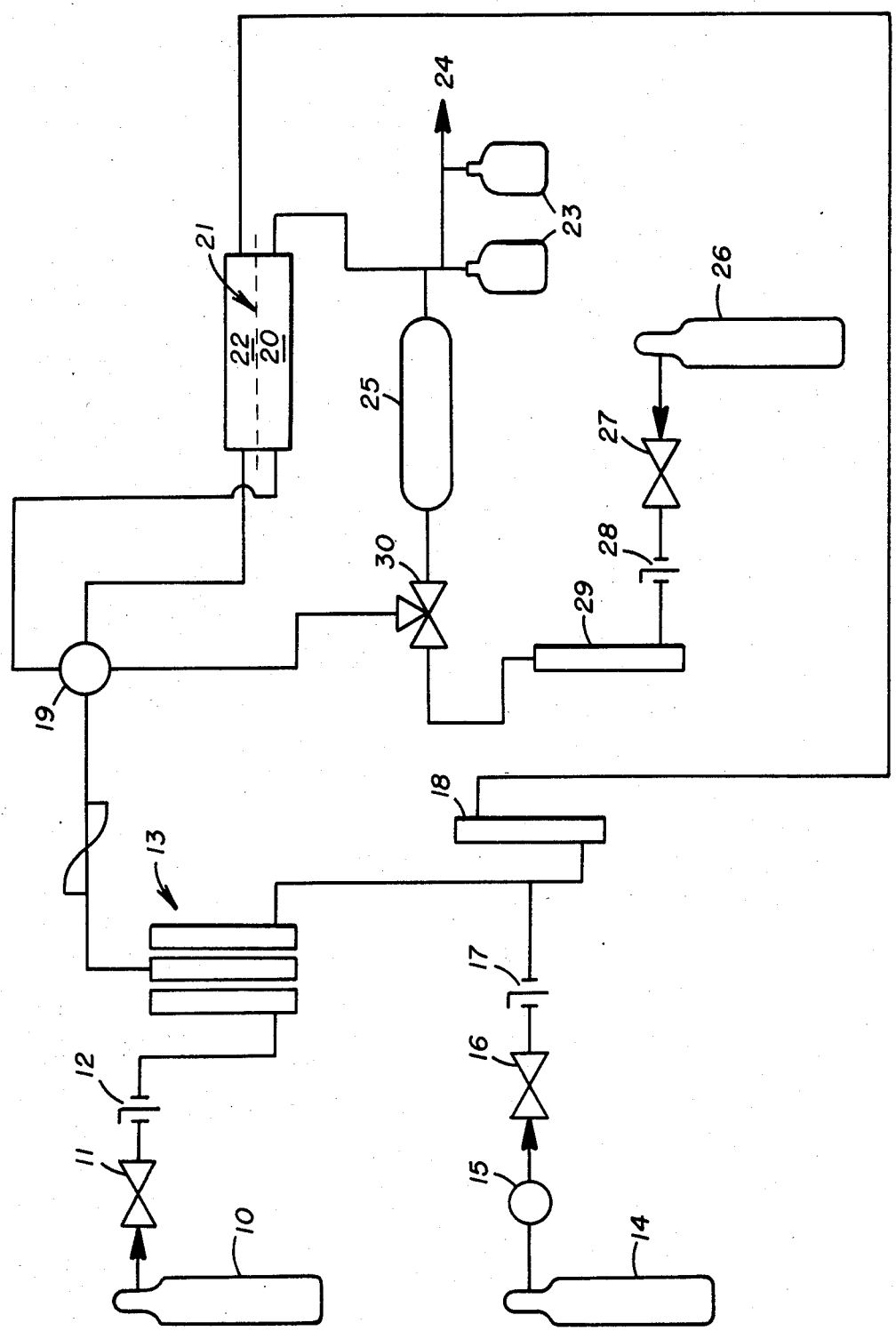

SYSTEM FOR ANALYZING PERMEATION OF A GAS OR VAPOR THROUGH A FILM OR MEMBRANE

BACKGROUND OF THE INVENTION

This invention relates to a system adapted for analyzing the permeation of a gas or vapor through a film or membrane, more particularly the rate of such permeation.

Some films are used to prevent or inhibit the permeation of certain gases either out of an environment, or into a certain environment. Membranes are often used to separate certain components, in some cases certain gases. Both membranes and films are used to either prevent the permeation of a certain gas, or separate gas mixtures. The rate of permeation of a certain gas through such film or membrane is a critical factor. Films used to prevent the permeation of one component either out of or into an environment find use in many areas; barrier packaging, agricultural films, industrial hygiene, and the like.

In one particular embodiment, agricultural films are used to minimize the loss of soil fumigant to the atmosphere by providing a physical barrier to the fumigant. To determine the efficacy of such films in such use, the rate of permeation of the particular fumigant through the film is critical. A device built by M. J. Kolbezen has been developed for measuring such rates of permeation. See Kolbezen et al *Pesticide Science*, 3, 67-71 (1972); and Kolbezen et al *Pesticide Science,* 3, 73-80 (1972) (both incorporated herein by reference in relevant parts). Within the agricultural films industry this device and the measurement of the rate of permeation that it affords, now called the Kolbezen, are recognized as the standard in the art.

The Kolbezen device suffers from some deficiencies, in that the Kolbezen device allows for the measurement of a rate of permeation wherein the pressure on both sides of the film are equal. In many applications the pressure on either side of the film is different thereby effecting the rate of permeation. Further, the Kolbezen device measures the rate of permeation wherein the temperature on both sides of the film is equivalent. In may environments the temperature on either side of the film is significantly different. The failure to account for such differences results in the measurement of permeation rates in an environment which does not reflect actual usage conditions.

What is needed is a means for measuring the rate of permeation of a gas or vapor through a film or membrane wherein the pressure on either side of the membrane or film is different. What is further needed, is a method for measuring the rate of permeation of a gas or vapor through a film or membrane wherein the temperature on either side of the film or membrane is different.

SUMMARY OF INVENTION

The invention is a system for measuring the permeation of a vapor or gas through a film or membrane, the system comprising (a) a means for introducing a test gas or vapor;
(b) a means for regulating the flow and pressure of the test gas or vapor connected to the means for introducing the test vapor or gas;
(c) a means for introducing a bulk gas;
(d) a means of regulating the flow and pressure of the bulk gas connected to the means for introducing the bulk gas;
(e) a means for combining the test vapor or gas and a portion of the bulk gas and adapted for controlling the pressure and flow of such said combining means connected to the means for controlling the flow and pressure of the test vapor or gas and further connected to the means for controlling the flow and pressure of the bulk gas;
(f) a test cell comprising
  (i) a first chamber connected to the means for combining test gas or vapor and bulk gas wherein the chamber is adapted for passing such combined test gas or vapor and bulk gas through the chamber at a rate such that a portion of the test gas or vapor can permeate through a film or membrane;
  (ii) a second chamber connected to the means for regulating the flow and pressure of the bulk gas wherein the second chamber is adapted for flowing bulk gas through the chamber and for receiving test gas or vapor which permeates through a membrane or film;
  (iii) a means for securing a membrane or film such that the film or membrane separates the first and second chamber;
  wherein the pressure in the first chamber is regulated by the means for regulating the flow and pressure of the combined test gas or vapor and the bulk gas; and the pressure in the second chamber is regulated by the means for regulating the flow and pressure of the bulk gas;
(g) a means for analyzing the composition of a gas or vapor specially adapted for measuring the concentration of test gas or vapor, connected to the second chamber of the test cell or the means for regulating the flow and pressure of the combined test gas or vapor and bulk gas;
(h) a means for regulating flow of gas or vapor between the first chamber of the test cell, the means for analyzing the compostion of a gas or vapor, and the means for regulating the flow and pressure of the combined test gas or vapor and bulk gas.

BRIEF DESCRIPTION OF THE FIGURE

The FIGURE is a flow diagram of one embodiment of this invention.

DETAILED DESCRIPTION OF INVENTION

Film or membrane as used herein refers to any substance which may be used to inhibit or restrict the permeation of a gas or vaporous component from one side of the film or membrane to the other. Examples of such films include barrier packaging films; agricultural films; gloves used for medical, surgical, and industrial hygiene; and the like. Examples of membranes include those membranes useful for separating one gas from another, for example, an impurity from air, an impurity from natural gas, and the like.

Test gas refers herein to any gas in a vaporous or gaseous condition which has sufficient energy to permeate through a film or membrane. Such test gases may include soil fumigants, hazardous industrial compounds, undesirable components of a gaseous stream, water vapor, and the like. In the field of argricultural fumigants, one fumigant for which agricultural films are commonly used is methyl bromide.

The means for introduction of a test vapor or gas into the system can involve any method or device of introducing a test gas or vapor into the system. In one embodiment a cylinder containing a portion of the test gas can be connected defined herein. In another embodiment, the test gas is introduced by injection into the system with a syringe.

The means for regulating the flow and pressure of the test vapor or gas is connected to the means for introduction of the test vapor or gas, and can be any means for regulating the flow of such test gas or vapor and for regulating the pressure of such test gas or vapor. Further, it is preferable that such means be capable of adjusting the flow and pressure so as to result in a low partial pressure of a test gas or vapor in a sample stream. In one embodiment, the means for regulating the test gas comprises a restrictor which functions to restrict the flow of the test gas to the remainder of the system. Such means can optionally include a rotameter for restricting the flow further and adjusting the pressure of such test gas or vapor. Optionally, such means for regulating the flow and pressure of the test gas can include a regulator. The use of the regulator or need thereof, is dependent upon the means for introduction of the gas or vapor. Wherein the means for introduction of the test gas or vapor provides such at a high pressure the regulator can be used to reduce the pressure of the test gas to a level which is acceptable for analysis.

Bulk gas refers herein to the remainder of the gaseous component in the analyzer system, such bulk gas functions to define a system which more closely reflects that system wherein the film or membrane will be used. Bulk gas can be any gas or mixture of gases that can be the major component of a gaseous or gaseous vaporous mixture from which the concentration of the test gas in such mixture can be measured. In such system the concentration of the test gas is closely related to the concentration it will be found in the system of use. Bulk gas can be instrument grade air, oxygen, nitrogen, natural gas, the gaseous waste stream from a plant, or the like. The means for introducing a bulk gas can be any means for introducing the bulk gas into the rest of this system as described hereinafter. In one embodiment, the means for introducing the bulk gas can be a tank or cylinder of such bulk gas connected to the system in some manner. In another embodiment, the test gas is introduced by injection into the system with a syringe.

The means for regulating the flow or pressure of the bulk gas is connected to the means for introducing the bulk gas. Such means for regulating the flow or pressure of the bulk gas can be any means which regulates the flow and pressure of the bulk gas, and which provides the bulk gas to the rest of the system at flows and pressures suitable for measuring the rate of permeation of the test gas through the membrane or film. In one embodiment, such means comprises a restrictor which functions to restrict the flow of the bulk gas to the rest of the system in a controllable manner. Such means may further comprise a rotameter which further restricts the flow of gas to the rest of the system and adjusts the pressure of the bulk gas to the desired pressure level. The rotameter functions as a means for controlling the pressure in one portion of the test cell, as described hereinafter. Optionally, the means for regulating the flow and pressure of the bulk gas can include a regulator, which functions to regulate the pressure between the means for introducing the bulk gas and the restrictor, so as to reduce the pressure from such means for introducing the bulk gas. The regulator is highly desirable where a means for introducing the bulk gas introduces such bulk gas at relatively higher pressures then the pressures at which the permeation of the test gas through the film or membrane is measured.

The means for combining the test vapor or gas and a portion of the bulk gas can be any means which allows combination of the two streams, mixing to form a relatively homogenous mixture, and which is adapted to regulating the pressure and the flow of the mixed streams to the remainder of the system. Such means of combining the test vapor or gas and bulk portion of the bulk gas is connected to the means for regulating the flow and pressure of the test gas, and the means for regulating the flow and pressure of the bulk gas. This means functions to prepare a sample for analysis of the test gas in the desired concentration. In one embodiment, such means is a gas proportioner, which is a gas meter and mix rotameter. In one embodiment such gas proportioner is connected to the first restrictor adapted for restricting the flow of the test gas. In such embodiment, the gas proportioner is further connected to the means for controlling the flow and pressure of the bulk gas between the restrictor and rotameter.

The test cell comprises three elements. The first element is a first chamber which is connected to the means for combining the test gas or vapor and the bulk gas, and such chamber is adapted for passing such combined test gas or vapor and bulk gas through the chamber at a rate such that a portion of the test gas or vapor can permeate through a film or membrane. Such chamber has an inlet for the combined test gas or vapor and bulk gas and an outlet for bulk gas and nonpermeated test gas or vapor. The flow rate of the combined test gas or vapor and bulk gas should be such that the test gas or vapor has an opportunity to permeate through the film or membrane. This chamber, can be half of a cylinder, for which the other half is the second chamber to be described hereinafter. The second element of the test cell is a second chamber which is connected to the means for regulating the flow and pressure of the bulk gas, and said second chamber is adapted for flowing bulk gas through the chamber and for receiving test gas or vapor which permeates through the membrane or film. The second chamber has an inlet which introduces bulk gas and an outlet which removes bulk gas and any permeated test gas or vapor. The flow rate through the second chamber should be such a flow as to reflect the environment for which the film or membrane would be used in. In one embodiment, the flow rate through the second chamber should be substantially the same as the flow rate through the first chamber. This second chamber can be a portion of a cylinder such that when combined with the first chamber a cylinder is formed.

A third element of the test cell is the means for securing the film or membrane between the first chamber and the second chamber. Such means for securing the film or membrane must be such that the entire area between the first and second chamber is separated by such film or membrane. The separation should be such that only the gases or vapors which will permeate through the film or membrane can communicate between the two chambers. When the two chambers form a cylinder the means for securing the membrane can be any means which allows the two chambers to fit together over the film or membrane. It is preferable that a gasket be present between the interface of the two chambers and each side of the film or membrane. In one preferred embodiment such a gasket can be a Teflon ® gasket. The test cell is preferably made of a material inert to the bulk gas and test gas or vapor. The choice of such a material is dependent upon the particular system to be tested, and such choice is well within the skill of the art. The choice of the size and shape of the particular cell is dependent upon the membrane used, and the system to be tested, such design is well within the skill of the art.

Optionally, the test cell is contacted with a means for transferring heat. In one embodiment one means for transferring heat can be contacted with the entire test cell, in this embodiment the temperature between the two chambers of the test cell would be substantially the same. In one embodiment, each test chamber would be contacted with a separate means for transferring heat. In this embodiment, the temperature of each chamber can be separately regulated so as to allow for a temperature gradient across the film or membrane.

Such means for transferring heat can be any means which allows the transfer of heat either to or from the test cell. One such means is to provide a circulating bath of water and an alkalene glycol, such as ethylene glycol, around either the entire test cell or each chamber separately. In one embodiment, the test cell can be designed so as to comprise two portions, one portions comprising a hollow chamber which forms half a cylinder such chamber surrounded by a chamber through which a heat transfer medium can be circulated. Each chamber can then contain a gasket around the outside portion so that when a membrane is fitted between the two chambers a sealed cylinder can be formed.

The means for analyzing the composition of a gas or vapor is specially adapted for measuring the concentration of test gas or vapor in the bulk gas. This means can be any means which can determine the composition of the gas or vapor. In one embodiment such means is an analytical device adequate for measuring the concentration of the test gas or vapor in a gaseous or vaporous stream. In one embodiment such analytical device can be a gas chromatograph. In a preferred embodiment, such means is capable of measuring the concentration on a continous, or semi-continous basis. Such means for analyzing a gaseous or vaporous composition is connected at different times during the operation of the system to the means for combining the test gas or vapor with the bulk gas, with the second chamber of the test cell, and optionally with the means for introducing a calibration gas into the system, as hereinafter described. When connected to the means for introducing a calibration gas, the means for analyzing the composition of a gaseous or vaporous composition is calibrated so as to provide a standard for further analysis. When connected to the means for combining the test gas or vapor with the bulk gas, the means for analyzing the gaseous or vaporous composition is measuring the concentration of the test gas or vapor in the feed stream to the first chamber of the cell. When connected to the second chamber of the test cell, the means for analysis is measuring the concentration of the test gas or vapor in the second cell, at a particular point in time. A series of such measurements, allows the calculation of the rate of permeation through the film or membrane.

The means for regulating the flow of the gas or vapor between or to the means for analyzing, is adapted for adjusting the flow of the feed combined test gas or vapor and bulk vapor between the means for analyzing, the first chamber of the test cell, and for regulating the flow of the bulk gas to which permeating test gas is added from the second chamber of the test cell.

A source for introduction of a calibration gas or vapor, can be any means which provides a standard to the analyzer so as to calibrate the analyzer with respect to the test gas or vapor. In one such embodiment, such means can involve a cylinder of a calibration gas with a known concentration of said gas. In another embodiment, the calibration gas is introduced by injection into the system with a syringe. Such means for introduction of calibration gas to the system is connected to the analyzer through a means for regulating the flow and pressure of the calibration gas. Such means for regulating the flow of calibration gas can be any means which can adjust both the flow and pressure of the calibration gas to the analyzer. In one embodiment, such means comprises a restrictor connected to the means for introducing the calibration gas, wherein the restrictor is adapted for regulating the flow of such calibration gas. In another embodiment, connected to the restrictor is a rotameter adapted for further regulating the flow of the calibration gas and the pressure of the calibration gas. Optionally, the means for introduction of the calibration gas may be connected to a regulator before such calibration gas is introduced to a restrictor, so as to reduce the pressure of the calibration gas introduced to the system. The optional regulator is used wherein the source of the calibration gas is at high pressure, or a substantially higher pressure than it is introduced to the analyzer.

Optionally, the outlet for the means for analysis and the first chamber of the test cell can be routed through a gas scrubbing system, wherein it is desirable to remove one or more of the components of either stream before disposing of the remainder of the stream.

The system claimed herein may be further understood with reference to the FIGURE. The numeral (10) refers to a first cylinder of test gas or vapor, this cylinder (10) is connected to a valve (11) adapted for introducing the test gas or vapor to the system. The first cylinder (10) is connected to the valve (11) through a restrictor (12), which is adapted for regulating the flow of the test gas to the remainder of the system. The first restrictor (12) is thereafter connected to a gas proportioner (13) and adapted for introducing the test gas into the gas proportioner (13). A second cylinder (14) contains the bulk gas. The second cylinder (14) connects into a regulator (15), wherein the regulator (15) is adapted for reducing the pressure of the gas from the second cylinder (14) to the remainder of the system. The regulator (15) thereafter is connected to a valve (16) adapted for controlling the introduction of bulk gas to the system. Connected to such valve (16) is a second restrictor (17) adapted for regulating the flow of bulk gas to the system. The second restrictor (17) is further connected to the gas proportioner (13), so as to introduce a portion of the bulk gas into the gas proportioner (13) and allow the combination of such bulk gas with the test gas. The restrictor (17) is further connected to a rotameter (18), adapted for regulating the pressure and flow of the bulk gas to the remainder of the sytem. The gas proportioner (13) is alternatively connected by way of a 4-way valve (19) to either the first chamber of the test cell (20), or to the gas chromatograph (25) so as to allow analysis of the composition of the test gas, mixed bulk gas and/or vapor stream. The first chamber (20) is adapted for receiving and flowing through said chamber (20) the combined test gas or vapor and bulk gas, under conditions such that the test gas can permeate through the membrane (21) to the second chamber (22). The outlet of the first chamber (20) is connected to a scrubbing system (23) and thereafter to a vent to the atmosphere (24). The rotameter (18) is connected to the inlet at the second chamber of the test cell (22) so that bulk gas may be flowed through the second chamber (22) so as to receive any test gas permeating through membrane (21) from the first chamber (20). The second chamber of the test cell (22) is connected by way of the 4-way valve (19) to the gas chromatograph (25), so as to allow the analysis of the bulk gas leaving the second chamber (22) for the concentration of test gas or vapor therein.

A third cylinder (26) provides a source of calibration gas which is connected to a valve (27) adapted for introducing the calibration gas to the system. The cylinder of calibration gas (26) is connected by valve (27) to a third restrictor (28) adapted for controlling the flow of the calibration gas to the gas chromatograph (25). The restrictor (28) is further connected to a second rotameter (29) adapted for regulating the pressure and further regulating the flow of the calibration gas to the chromatograph (25). The rotameter (29) is connected through a 3-way valve (30) to the chromatograph (25), said 3-way valve (30) adjusts the flow between the 4-way valve (19) and the rotameter (29) to the gas chromatograph (25). The gas chromatograph (25) has an outlet which is connected to the scrub system (23) and thereafter vented from the system (to the atmosphere) by (24).

The system described hereinbefore is useful to measure the permeation of a test gas through any film or membrane for which its permeation properties with respect to such test gas can be analyzed. This can be used to measure the permeation of any vapor or gas which may permeate through a membrane or film, for example, argricultural chemicals, such as methyl bromide. In one embodiment, the system is used wherein such vapor or gas is found in a concentration of 75,000 parts per million or below.

This system can be used to measure the permeation of a test gas through a membrane or film wherein the pressure on either side of the film or membrane is different. In the embodiment described hereinbefore, the pressure to the first chamber of the test cell is regulated by the gas proportioner, and the pressure to the second chamber of the cell is regulated by the first gas rotameter. By allowing for the measure of permeation through a membrane or film wherein the pressure is different on either side of the membrane or film, the permeation rates can be examined in the system which more readily reflects the environment under which the film or membrane will be used. In one embodiment, the rate of permeation through membrane or film can be measured wherein the temperature on either side of the membrane or film is different.

The flow through the first chamber and the flow through the second chamber can be monitored through the use of a soap bubble tube and a stop watch.

In the embodiment described hereinbefore, the gas chromatograph is calibrated with a standard gas adjusting the 3-way valve (30) so as to connect the cylinder of calibration gas (26) to the gas chromatograph (25). Thereafter the pure test gas and bulk gas are mixed in the gas proportioner (13) and samples of such combined gases are monitored by the gas chromatograph (25), when the valves (19) and (30) are adjusted to allow the flow of mixed gas from the gas proportioner directly to the gas chromatograph. This combined stream is monitored by the gas chromatograph until the peak height achieved approximates the calibration gas response. The actual concentration of test gas can be calculated from the calibration peak, assuming a linear response of the detector. The valve (19) is then adjusted to allow a portion of the mixed gas to enter the first chamber of the test cell (20), while a portion of bulk gas is allowed to flow through the second chamber of the cell (22). It is preferable that the flow of the mixed gas, and the bulk gas be counter-current over either side of the film or membrane and at the same flow rate. The gas exiting the second chamber of the test cell (22) is sampled at regular intervals, for example 4 to 6 minutes by the gas chromatograph. The sampling continues until an equilibrium is reached, wherein the peak heights remain constant. One equilibrium is reached when the standard permeation can be calculated. Standard permeation rate units are: ml/hr/m$^2$/ml/lit/ or, volume of pure test gas crossing the film or membrane per hour, per meter of area of the film or membrane exposed per unit concentration of the test gas in m/liter of bulk gas. This is referred to as $R_k$.

SPECIFIC EMBODIMENT

Description of Apparatus

A methyl bromide supply tank is fitted with a parker ball valve containing a stainless steel frit designed to reduce flow to 25 ml/minute under a 30 psig load. An instrument air supply is fitted similarly, except a two-stage regulator feeds 30 psig to the parker valve. Instrument air is fed through a calibrated Matheson ® manometer to the top side of the test cell so that flow can be maintained identically with the sample gas flow rate. Instrument air also feeds into the gas mixing chamber (Matheson ® 7372t gas proportioner, discharge rate: 20 ml/minute) where it combines with pure methyl bromide to prepare the test gas mixture. The gas proportioner is composed of two separate rotameters (Matheson ® model 7442-610), that feed into a static mixing chamber, the output of which is feed into a 4-way selector valve so that the test gas can be sampled directly to the GC until the desired mixture concentration is obtained, and then switched over to feed directly into the lower side of the cell, allowing the instrument air flowing in the upper side to be sampled by the gas chromatograph. Prior to mixed gas preparation, a purchased methyl bromide standard gas is entered into the GC for calibration purposes. The cell is constructed of solid brass with an exposed surface area of 0.024 meters squared. Cooling ports for both top and bottom allow for variable temperature experiments, as well, a temperature differential can be maintained. The analyzer is a Beckman ® 6710 gas chromatograph. A soap bubble tube flow meter is used to calibrate all flows. Complete analysis time, between automatic injection times, is 160 seconds. Injection time is 80 seconds. After injection time is complete, the stripper is washed with a back flow of carrier gas to ensure low volatile components do not accumulate in the sample column. Column tubing is ⅛ inch stainless steel. Sample load is about 5 microliters. All tubing and fittings are stainless steel. Two films of known permeation rate (as determined by M. Kolbezen), are analyzed by the instruments described here and before. Sample one was measured by kolbezen to have 5.4 $R_k$ at 30° centigrade and 11.5 $R_k$ at 50° centigrade. Sample 2 values were given at 9.7 $R_k$ at 30° centigrade and 20.1 $R_k$ at 50° centigrade. The sample 1 film is a blend of 10% high density polyethylene film, 10% low density film and 80% of blend linear low density film.

The sample 2 film is a low density polyethylene film.

In the test run with the above described apparatus the test cell is allowed to come to equilibrium at 30° centigrade, as evidenced by equivalant reproducible peak heights, and thereafter the cell temperature is raised to 50° centigrade, thereafter the samples are allowed to come to equilibrium as exemplified by the peak heights. The conditions and results for each experiment are contained in the table.

| Run | Concentration PPM | Temp °C. | Flow ml/min | Permeation $R_k$ |
|---|---|---|---|---|
| | FILM 1[1] | | | |
| 1 | 18,500 | 30 | 20 | 6.8 |
| | 18,500 | 50 | 26 | 11.9 |
| 2 | 7,882 | 30 | 18 | 6.8 |
| | 7,882 | 50 | 18 | 13.0 |
| 3 | 4,472 | 30 | 13 | 6.1 |
| | 4,472 | 50 | 13 | 13.0 |
| | FILM 2[2] | | | |
| 1 | 13,600 | 30 | 20 | 10.3 |
| | 13,600 | 50 | 20 | 19.9 |
| 2 | 11,400 | 30 | 20 | 10.1 |
| | 11,400 | 50 | 20 | 21.2 |
| 3 | 9,500 | 30 | 20 | 9.7 |
| | 9,500 | 50 | 20 | 20.8 |

[1]Published Kolbezen values - 5.4 at 30° C., and 11.5 at 50° C.
[2]Published Kolbezen values 9.7 at 30° C. and 20.1 at 50° C.

The average of the values on film 1 at 30° C. is 6.6 with a standard deviation of 0.4. The average of the values on film 1 at 50° C. is 12.6 with a standard deviation of 0.6. The average of the values on film 2 at 30° C. is 10.0 with a standard deviation of 0.4. The average of the values on film 2 at 50° C. is 20.6 with a standard deviation of 0.4.

What is claimed is:

1. A system for measuring the permeation of a vapor or gas through a film or membrane, the system comprising
    (a) a means for introducing a test gas or vapor;
    (b) a means for introducing a bulk gas;
    (c) a restrictor adapted for regulating the flow of the test gas or vapor which is connected to the means for introducing the test gas or vapor;
    (d) a second restrictor which is adapted for regulating the flow of the bulk gas which is connected to the means for introducing the bulk gas;
    (e) a gas proportioner adapted for combining the test gas or vapor with a portion of the bulk gas and for regulating the flow and pressure of the combined test gas or vapor and a portion of the bulk gas connected to the first restrictor and the second restrictor;
    (f) a rotometer adapted for controlling the flow and pressure of the bulk gas not combined with the test gas or vapor;
    (g) a test cell comprising
        (i) a first chamber inlet connected to the gas proportioner wherein the first chamber is adapted for passing combined test gas or vapor and bulk gas through the first chamber at a rate such that a portion of the test gas or vapor can permeate through a film or membrane;
        (ii) a second chamber connected to the rotometer wherein the second chamber is adapted for flowing bulk gas through the second chamber and for receiving test gas or vapor which permeates through the membrane or film;
        (iii) a means for securing the membrane or film between the first and second chambers such that any test gas or vapor which permeates through the membrane from the first chamber will pass into the second chamber;
    (h) a means for introducing a calibration gas,
    (i) a restrictor adapted for controlling the flow and pressure of the claibration gas;
    (j) a second rotometer adapted for controlling the flow of the calibration gas;
    (k) a gas chromatograph adapted for analyzing the concentration of test gas or vapor in a sample, which is connected to the second chamber of the test cell, the gas proportioner, or the second rotometer adapted for regulating the flow of the calibration gas;
    (l) a means for regulating the flow of combined test gas or vapor and bulk gas between the first chamber of the test cell and the gas chromatograph, and the flow of bulk gas containing test gas or vapor which has permeated through the membrane or film to the second chamber, from the second chamber to the gas chromatograph;
    (m) a first means for transferring heat which is in contact with the first chamber and is adapted for regulating the temperature of the first chamber; and
    (n) a second means for transferring heat which is in contact with the second chamber and is adapted for regulating the temperature of the second chamber.

2. A system for measuring the permeation of a test gas or vapor through a film or membrane, the system comprising
    (a) a means for introducing a test gas or vapor;
    (b) a means for regulating the flow and pressure of the test gas or vapor connected to the means for introducing the test gas or vapor;
    (c) a means for introducing a bulk gas;
    (d) a means of regulating the flow and pressure of the bulk gas connected to the means for introducing the bulk gas;
    (e) a means for combining the test gas or vapor and a portion of the bulk gas and adapted for controlling the pressure and flow of such, said means for combining the test gas or vapor and a portion of the bulk gas is connected to the means for regulating the flow and pressure of the test gas or vapor and further connected to the means for regulating the flow and pressure of the bulk gas;
    (f) a test cell comprising
        (i) a first chamber connected to the means for combining test gas or vapor and a portion of the bulk gas wherein the first chamber is adapted for passing combined test gas or vapor and a portion of the bulk gas through the first chamber at a rate such that a portion of the test gas or vapor can permeate through a film or membrane;
        (ii) a second chamber connected to the means for regulating the flow and pressure of the bulk gas wherein the second chamber is adapted for flowing bulk gas through the chamber and for receiving test gas or vapor which permeates through the film or membrane;

(iii) a means for securing the film or membrane such that the film or membrane separates the first and second chamber;

wherein the pressure in the first chamber is regulated by the means for combining the test gas or vapor and a portion of the bulk gas; and the pressure in the second chamber is regulated by the means for regulating the flow and pressure of the bulk gas;

(g) a means for analyzing the composition of a gas or vapor specially adapted for measuring the concentration of test gas or vapor, connected to the second chamber of the test cell or the means for combining the test gas or vapor and a portion of the bulk gas;

(h) a means for regulating flow of the combined test gas or vapor and a portion of the bulk gas, adapted for regulating the flow of combined test gas or vapor and a portion of the bulk gas from the means for combining the test gas or vapor and a portion of bulk gas between the first chamber of the test cell and the means for analyzing the composition of a gas or vapor.

(i) a first of transferring heat in contact with the first chamber adapted for regulating the temperature of the first chamber; and (j) a second means of transferring heat in contact with the second chamber adapted for regulating the temperature in the second chamber.

3. The system of claim 2 which further comprises a means for introduction of a calibration gas or vapor; and a means for regulating the flow and pressure of the calibration gas adapted for regulating the flow of calibration gas between the means for the introduction of the calibration gas and the means for analyzing the composition of a gas or vapor.

4. The system of claim 3 wherein the means for regulating the flow and pressure of the test gas or vapor comprises a restrictor.

5. The system of claim 4 wherein the means for regulating the flow and pressure of the test gas or vapor further comprises a regulator adapted for reducing the pressure of the test gas or vapor flowing from the source of the test gas or vapor.

6. The system of claim 4 wherein the means for regulating the flow and pressure of the bulk gas comprises a restrictor and a rotometer.

7. The system of claim 6 wherein the means for regulating the flow and pressure of the bulk gas further comprises a regulator adapted for reducing the pressure of the bulk gas from means for introducing a bulk gas.

8. The system of claim 7 wherein the means for combining the test gas or vapor and a portion of the bulk gas comprises a gas proportioner.

9. The system of claim 8 wherein the means for analyzing the composition of a gas or vapor comprises a gas chromatograph.

10. The system of claim 9 wherein the means for regulating the flow between the first chamber of the test cell, second chamber of the test cell, the means for analyzing the composition of a gas or vapor and the means for combining test gas or vapor and a portion of the bulk gas is a 4-way valve.

11. The system of claim 10 wherein the means for regulating the flow and pressure of the calibration gas comprises a restrictor and a rotometer.

* * * * *